(12) United States Patent
Brune et al.

(10) Patent No.: US 8,034,377 B2
(45) Date of Patent: Oct. 11, 2011

(54) DHA ESTERS AND USE THEREOF IN TREATMENT AND PREVENTION OF CARDIOVASCULAR DISEASE

(75) Inventors: Frederique Brune, Gif S/Yvette (FR); André Delhon, Castres (FR); Jean Gardette, Neuilly sur Seine (FR); Jean François Patoiseau, Castres (FR); Alain Marty, Toulouse (FR); Etienne Severac, Pibrac (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 32 days.

(21) Appl. No.: 12/305,162

(22) PCT Filed: Jun. 22, 2007

(86) PCT No.: PCT/EP2007/056277
§ 371 (c)(1),
(2), (4) Date: May 15, 2009

(87) PCT Pub. No.: WO2007/147899
PCT Pub. Date: Dec. 27, 2007

(65) Prior Publication Data
US 2009/0312354 A1 Dec. 17, 2009

(30) Foreign Application Priority Data
Jun. 23, 2006 (FR) ..................................... 06 05649

(51) Int. Cl.
*A61K 9/48* (2006.01)
*A61K 31/435* (2006.01)

(52) U.S. Cl. ........................................ 424/452; 514/277
(58) Field of Classification Search .................. 424/452; 514/277
See application file for complete search history.

(56) References Cited

U.S. PATENT DOCUMENTS

| | | | |
|---|---|---|---|
| 4,619,829 | A | 10/1986 | Motschan |
| 5,760,081 | A | 6/1998 | Leaf et al. |
| 5,919,815 | A | 7/1999 | Bradley et al. |
| 2003/0050341 | A1 | 3/2003 | Bydlon et al. |
| 2004/0077723 | A1 | 4/2004 | Granata et al. |
| 2005/0171200 | A1 | 8/2005 | Calder et al. |

FOREIGN PATENT DOCUMENTS

| | | |
|---|---|---|
| EP | 0909183 B1 | 8/2004 |
| EP | 1 157 692 B1 | 10/2005 |
| GB | 1170132 A | 11/1969 |
| JP | 59-067263 A | 4/1984 |
| JP | 59-067264 A | 4/1984 |
| JP | 60-034947 A | 2/1985 |
| WO | WO 96/34868 A1 | 11/1996 |
| WO | WO-01/46115 A1 | 6/2001 |
| WO | WO-2004/047835 A1 | 6/2004 |
| WO | WO 2004/091317 A1 | 10/2004 |
| WO | WO-2004/091603 A1 | 10/2004 |

OTHER PUBLICATIONS

Tsujita-Kyutoku Miki, et al. "Conjugated docosahexaenoic acid suppresses KPL-1 human breast cancer cell growth in vitro and in vivo: potential mechanisms of action", Breast Cancer Research. Com [Online] 2004, 6: pp. 291-299.
Tuoya et al. "Apoptosis induction by dohevanil, a DHA substitutive analog of capsaicin, MCF-7 cells", Life Sciences 78, 2006, pp. 1515-1519.
Harvey D.J., "Picolinyl Derivatives for the Structural Determination of Fatty Acids by Mass Spectrometry: Applications to Polyenoic Acids, Hydroxy Acids, Di-Acids and Related Compounds", Biomedical Mass Spectrometry 1984 UK, vol. 11, n. 7, 1984, pp. 340-347 XP009078567.
Schmalzing G., et al. "Modulation of ATPase activities of human erthrocyte membranes by free fatty acids or phospholipase A2", [Medline] J. Member Biology, 1982; 69(1); pp. 65-76.
Swarts H.G., et al., "Binding of unsaturated fatty acids tp NA+, K(+)-ATPase leading to inhibition and inactivation" [Medline] Biochim Biophys Acta. May 9, 1990; 1024(1) pp. 32-40.
Swarts H.G., et al., "Effect of free fatty acids and detergents on H,K-ATPase. The steady-state ATP phosphorylation level and the orientation of the enzyme in membrane preparations" [Medline] Boichim Biophys Acta. Dec. 9, 1991; 1070(2), pp. 283-292.
Benais-Pont G., et al., "ω-3 Polyunsaturated fatty acids and ionizing radiation: combined cytoxicity on human colorectal adenocarcinoma cells", Nutrition 22 (2006), pp. 1-9.
Torres de Pinedo A., et al., "Efficient lipase-catalyzed synthesis of new lipid antioxidants based on a catechol structure", Tetrahedron 61 (2005), pp. 7654-7660 XP004971216.
Database CA [online] "3-Pyridylmethyl 4,7,10,13,16,19-docosahexaenoate", XP002419000, database accession No. 1053, 1985: 487779.
Chung B. H., et al., "Lipolysis-induced partitioning of free fatty acids to lipoproteins: effect on the biological properties of free fatty acids" Journal of Lipid Research, vol. 36, 1956-1970, Copyright 1995 by Lipid Research Inc.
Tsuda Hiroyuki, et al. "Cancer Prevention by Natural. Compounds" Drug Metab. Pharmacokin 19(4), (2004), pp. 245-263.

(Continued)

*Primary Examiner* — Andrew D. Kosar
(74) *Attorney, Agent, or Firm* — Birch, Stewart, Kolasch & Birch, LLP

(57) ABSTRACT

The present invention relates to a docosahexaenoic acid ester with an alcohol chosen among the group-B vitamins or provitamins, advantageously comprised by: nicotinyl alcohol of the following formula (I), panthenol of the following formula (II), and inositol of the following formula (III) or with isosorbide of the following formula (IV) or isosorbide mononitrate of the following formula (V). It also relates to a method of preparation of same, a pharmaceutical composition comprising same and the use of same in the treatment or prevention of cardiovascular disease, in particular auricular fibrillation.

13 Claims, 1 Drawing Sheet

OTHER PUBLICATIONS

Figure 1:
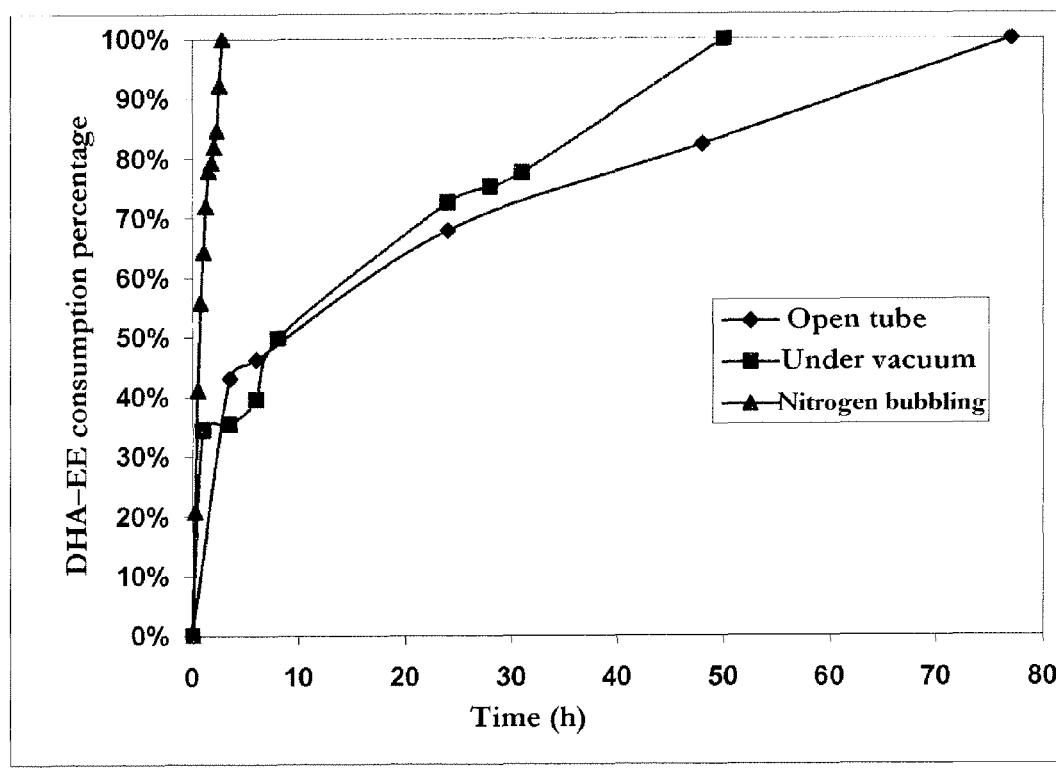

Maheo Karine, et al., "Differential sensitization of cancer cells to doxorubicin by DHA: A role for lipoperoxidation", Free Radical Biology & Medicine 39 (2005), pp. 742-751.

Mezoul G., et al. "Enzyme-Catalyzed Synthesis of Aliphatic Polyesters in Organic Media: Study of Transesterification Equilibrium Shift and Characterization of Cyclic Compounds", Journal of Polymer Science: Part A: Polymer Chemistry, vol. 33, (1995), pp. 2691-2698. XP-002418771.

Definition of B-Vitamin from Wikipedia (http:en.wikipedia.org/wiki/ Vitamin_B).

Definition of Inositol from Wikipedia (http:en.wikipedia.org wiki/Inositol).

Humeau C., et al., "Enzymatic synthesis of fatty acid ascorbyl esters", Journal of Molecular Catalysis B: Enzymatic 5 (1998), pp. 19-23. XP-002418770.

Bougnoux P., et al., "Diet, Cancer and the Lipidome", Cancer Epidemiol Biomarkers Prev., 2006; 15(3), Mar. 2006, pp. 416-421.

Kanorskii et al., "Influence of perindopril, rosuvastatin, or omega-3 polyunsaturated fatty acids on efficacy of antirecurrence therapy with sotalol in patients with persistent atrial fibrillation", Kardiologiia, vol. 47, No. 12 (2007) pp. 39-44.

Saravanan et al., "The Role of Omega-3 Fatty Acids in Primary Prevention of Coronary Artery Disease and in Atrial Fibrillation is Controversial", Journal of the American College of Cardiology, vol. 55, No. 4 (2010) pp. 410-411.

Saravanan, "Omega-3 fatty acid supplementation does not reduce risk of atrial fibrillation after coronary artery bypass surgery: a randomized, double-blind, placebo-controlled clinical trial", vol. 3, No. 1 (2009) pp. 46-53.

Attuel et al., "Failure in the Rate Adaptation of the Atrial Refactory Period: Its Relationship to Vulerability", International Journal of Cardiology, vol. 2, 1982, pp. 179-197, Elsevier Biomedical Press.

Calo et al., "N-3 Fatty Acids for the Prevention of Artial Fibrillation After Coronary Artery Bypass Surgery", Journal of the American College of Cardiology, vol. 45, No. 10, May 17, 2005, pp. 1723-1728, Elsevier Inc.

O'riordan, "Omego-3 Fatty Acids Prevent Atrial Fibrillation After CABG Surgery," May 5, 2005, http://www.theheart.org/article/457899.do.

Wijffels et al., "Atrial Fibrillation Begets Atrial Fibrillation: A Study in Awake Chronically Instrumented Goats", American Heart Association, Circulation, vol. 92, pp. 1954-1968.

Wirth et al., "Atrial Effects of the Novel K+-Channel-Blocker AVE0118 in Anesthnetized Pigs", Cardiovascular Research, vol. 60, 2003, pp. 298-306, Elsevier B.V.

French Preliminary Search Report and Written Opinion dated Mar. 30, 2011 for Application No. 1056560.

DHA ESTERS AND USE THEREOF IN TREATMENT AND PREVENTION OF CARDIOVASCULAR DISEASE

The present invention relates to docosahexaenoic acid (DHA) esters with alcohols chosen among the group-B vitamins or provitamins such as nicotinyl alcohol (B3), panthenol (B5) or isosorbide or isosorbide mononitrate, and in particular pyridin-3-ylmethyl docosahexaeneoate, and the use of same as a drug in the treatment and prevention of cardiovascular diseases.

The omega-3 polyunsaturated fatty acids, in particular EPA and DHA advantageously purified and concentrated in the form of ethyl ester, are known for their potential use in the treatment of certain cardiovascular diseases and in the modulation of corresponding risk factors. In particular, they are known in the treatment of hyperlipidemia, hypercholesterolemia and hypertension. Clinical trials carried out with formulations containing a high concentration of EPA and DHA ethyl ester on patients having suffered a myocardial infarction showed their effectiveness in reducing mortality and, in particular, sudden death. These results were attributed in part to a stabilizing effect on the cell membranes of ventricular cardiomyocytes, which prevent the appearance of malignant arrhythmia in the presence of ischemic myocytes, as seen in patients following an infarction or in experimental models which reproduce such conditions.

In addition, it is also known according to patent application WO 2004/047835 that DHA and EPA ethyl esters can be used to prevent auricular fibrillation. However, surprisingly, the inventors of the present application have discovered that DHA and EPA do not have the same effect on auricular fibrillation: DHA has a much greater effect on auricular fibrillation than does EPA. Thus, it is more advantageous to use DHA alone than a mixture of DHA and EPA in the treatment of auricular fibrillation and, undoubtedly, in the treatment of most cardiovascular disease.

The group-B vitamins covers hydrosoluble molecules belonging to very different chemical classes, but all having as a main function the capability to control enzymatic activities anywhere in the metabolism. These vitamins are named: thiamine (B1), riboflavin (B2), niacin (B3), panthothenic acid (B5), pyridoxine (B6), biotin (B8), folic acid (B9) and cyanocobalamin (B12).

The group-B vitamins and provitamins have advantages related to their functions. In particular, nicotinyl alcohol is the alcohol derived from nicotinic acid (vitamin B3). It is rapidly converted into nicotinic acid in the human body.

Nicotinic acid, also called niacin, is a water-soluble group-B vitamin that can be synthesized from tryptophan. However, the effective therapeutic doses for purposes of lowering cholesterol and lipids are higher than the quantities synthesized by the body. Thus, an oral supplement proves to be essential in targeting the lowering of cholesterol and/or triglycerides.

In terms of action mechanism, it is suspected that nicotinic acid inhibits the release of free fatty acids from adipose tissue, leading to a decrease in the fatty acid supply to the liver. Since fewer fatty acids are esterified into triglycerides, fewer will be incorporated in low-density lipoproteins (LDL), thus reducing LDL cholesterol levels. It has also been noted that nicotinic acid increases HDL cholesterol levels appreciably, most likely by inhibition of the catabolism of this form of HDL cholesterol.

In particular, nicotinic acid has a strong peripheral vasodilator effect. Thus, the intravenous injection of nicotinyl alcohol after its conversion into nicotinic acid leads to vasodilatation favorable to a drop in arterial pressure.

Nicotinic acid is widely used in therapies for lowering cholesterol and lipids.

It has also been shown that nicotinic acid can be combined with HMG-CoA reductase inhibitors, such as statins, for example, in cases in which the lowering of cholesterol by these HMG-CoA reductase inhibitors does not prove to be adequate. Such a combination can be beneficial when the benefits from the effects of each compound are sought, in particular lowering LDL cholesterol with statins and raising HDL cholesterol with nicotinic acid. In addition, nicotinic acid is suitable for the treatment of mixed dyslipidemia and is thus capable of influencing both cholesterol and triglyceride levels.

Panthenol is the alcohol derivative of pantothenic acid, more commonly known as vitamin B5. In the body, panthenol is transformed into pantothenic acid. Pantothenic acid then becomes a significant part of the compound coenzyme A, which is of particular interest in cellular metabolism. Indeed, it takes part in the metabolism of lipids, carbohydrates and proteins. Panthenol also participates in the formation of acetylcholine and adrenal steroids. It also acts in the detoxification of foreign bodies and in resistance to infection.

Inositol (vitamin B7) mobilizes fats by preventing their accumulation. It also has an anxiolytic effect, it stimulates the nervous system and the liver and it decreases blood cholesterol level. It is implicated in an increase in serotonin activity, control of intracellular calcium concentration, maintenance of cell membrane potential and cytoskeleton assembly.

Isosorbide, in particular isosorbide mononitrate, is a powerful peripheral vasodilator.

Accordingly, the present examples are docosahexaenoic acid ester with an alcohol chosen among:

nicotinyl alcohol of the following formula:

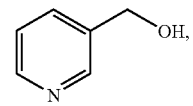

panthenol of the following formula:

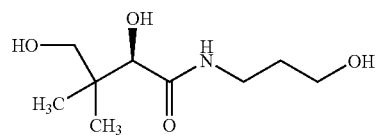

and inositol of the following formula:

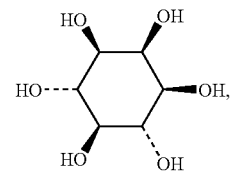

or with isosorbide of the following formula:

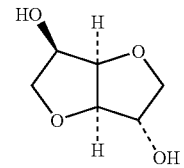

or isosorbide mononitrate of the following formula:

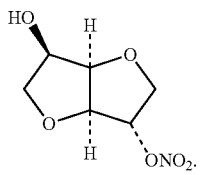

Advantageously pyridin-3-ylmethyl docosahexaeneoate of following general formula (1):

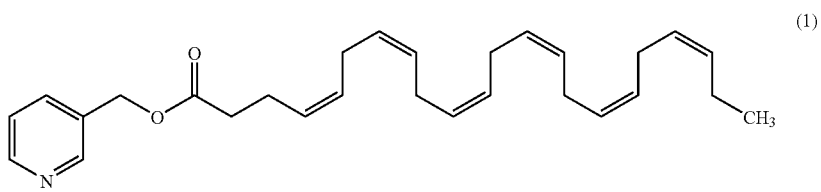

(1)

Surprisingly, the inventors have discovered that docosahexaenoic acid (DHA) esters with alcohols chosen among group-B vitamins or provitamins such as nicotinyl alcohol (B3), panthenol (B5), or with isosorbide or isosorbide mononitrate, in particular pyridin-3-ylmethyl docosahexaeneoate (docosahexaenoic acid (DHA) ester with nicotinyl alcohol), also have significant activity with respect to cardiovascular disease.

Thus, the present invention relates to a docosahexaenoic acid ester with an alcohol chosen among
panthenol of the following formula:

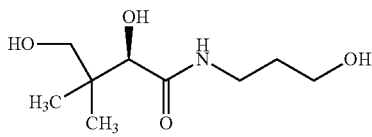

isosorbide of the following formula:

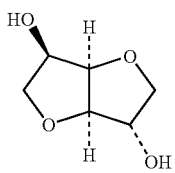

isosorbide mononitrate of the following formula:

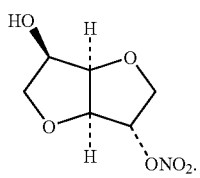

The present invention also relates to a method of preparation of the docosahexaenoic acid ester according to the present invention, by transesterification of docosahexaenoic acid ethyl ester with an alcohol chosen among the group comprised of, panthenol, isosorbide, isosorbide mononitrate and Transesterification can be carried out by methods well-known to those persons skilled in the art.

Advantageously, transesterification according to the present invention is carried out in the presence of a catalyst. Advantageously, such a catalyst is an alkaline-metal carbonate or alkaline-earth carbonate, advantageously $K_2CO_3$. Advantageously, the molar ratio of alkaline-metal carbonate or alkaline-earth carbonate to DHA ethyl ester is in the range of 1/1 to 6/1. Advantageously, the molar ratio of alcohol to DHA ethyl ester is in the range of 1/1 to 6/1, even more advantageously the molar ratio of nicotinyl alcohol to DHA ethyl ester is in the range of 1/1 to 6/1. Advantageously, the transesterification reaction is carried out in a solvent, advantageously chosen among dioxane or THF; advantageously THF is chosen. Advantageously, THF is degassed by nitrogen bubbling. Even more advantageously, the reaction mixture is heated under reflux, advantageously for at least 14 hours.

In another specific embodiment of the invention, the catalyst of the transesterification method according to the present invention is a lipase, advantageously a *Candida antarctica* lipase. In particular, the lipase is in an immobilized form. Advantageously, the lipase is Novozyme® sold by Novo Nordisk. Advantageously, the reaction takes place in a medium without solvent, or in a solvent such as 2-methyl-2-butanol or acetonitrile, advantageously in a medium without solvent in the case of nicotinyl alcohol and in a solvent in the case of panthenol. Advantageously, in the case of inositol, the solvent used is an ionic polar solvent such as 1-butyl-3-methylimidazolium BF4 or 1-butyl-3-methylimidazolium $C(CN)_2$. Advantageously, the reaction takes place at a temperature higher than room temperature, advantageously at 60° C.

Advantageously, ethanol is eliminated during the reaction, advantageously under a vacuum or by nitrogen bubbling, even more advantageously by nitrogen bubbling. In this way the conversion rate is increased, the reaction is accelerated and the parasitic hydrolysis reaction is eliminated.

Advantageously, the molar ratio of alcohol to DHA ethyl ester is between 1 and 5, advantageously between 1.5 and 4.5.

Advantageously, the reaction is carried out for between 1 hour and 100 hours, advantageously between 1 hour and 72 hours, advantageously between 1 hour and 48 hours, even more advantageously between 1 hour and 3 hours.

In another specific embodiment of the method according to the present invention, the transesterification reaction takes place in an anhydrous solvent, in a non-anhydrous solvent in the presence of a water trap such as, for example, lithium chloride, $MgCl_2$ or silica gel, or without solvent in a dry atmosphere. In this way the parasitic hydrolysis reaction is eliminated.

Advantageously, the transesterification reaction takes place with pure docosahexaenoic acid ethyl ester (at least 95% pure, available commercially or purified by methods well-known to those persons skilled in the art from a mixture of ethyl ester fatty acids) or with a mixture containing at least 70% molar DHA ethyl ester. In the case in which the DHA ethyl ester used is a mixture, it is advisable to purify the ester obtained following the transesterification reaction.

The present invention also relates to a pharmaceutical composition comprising the docosahexaenoic acid ester according to the present invention, and at least one pharmaceutically-acceptable excipient.

The pharmaceutical compositions according to the present invention can be formulated for administration in mammals, including man. Dosing varies according to the treatment and to the disease in question. These compositions are prepared in such a way as to be administered by oral, sublingual, subcutaneous, intramuscular, intravenous, transdermal, local or rectal route. In this case, the active ingredient can be administered in unit-dose forms or in a mixture with conventional pharmaceutical vehicles to animals or to humans. Suitable unit-dose administration forms include oral-route forms such as tablets, gelatin capsules, powders, granules and oral solutions or suspensions, sublingual and oral administration forms, subcutaneous, topical, intramuscular, intravenous, intranasal or intraocular administration forms and rectal administration forms.

When a solid composition is prepared in tablet form, the primary active ingredient is mixed with a pharmaceutical vehicle such as gelatin, starch, lactose, magnesium stearate, talc, gum arabic, silica or analogues. Tablets can be coated with sucrose or other suitable materials or they can be treated in such a way that they have delayed or extended activity and that they continuously release a predetermined quantity of the active ingredient.

A gelatin capsule preparation is obtained by mixing the active ingredient with a diluent and then pouring the mixture obtained into soft or hard gelatin capsules.

A preparation in syrup or elixir form can contain the active ingredient in conjunction with a sweetener, an antiseptic, as well as a flavoring agent and a suitable coloring agent.

Powders or granules that can be dispersed in water can contain the active ingredient in a mixture with dispersion agents, wetting agents or suspension agents, as well as with taste correctors or sweeteners.

Suppositories, which are prepared with binders that melt at rectal temperature, such as cocoa butter or polyethylene glycol, for example, are used for rectal administration.

Of use in parenteral (intravenous, intramuscular, etc.), intranasal or intraocular administration are aqueous suspensions, isotonic saline solutions or sterile injectable solutions containing pharmacologically-compatible dispersion agents and/or wetting agents.

The active ingredient can be also formulated in the form of microcapsules, optionally with one or more additives.

Advantageously, the pharmaceutical composition according to the present invention is for administration by oral or intravenous route, advantageously by intravenous route in the case of treatment postinfarction.

The pharmaceutical composition according to the present invention can include other active ingredients that give rise to a complementary or possibly synergistic effect. Advantageously, the pharmaceutical composition does not include EPA ester.

The present invention also relates to the docosahexaenoic acid ester according to the present invention, or the pharmaceutical composition according to the present invention, for use as a drug.

The present invention also relates to the docosahexaenoic acid ester according to the present invention, and to the pyridin-3-ylmethyl docosahexaeneoate according to the present invention, or the pharmaceutical composition according to the present invention, for use as a drug for the prevention and/or treatment of cardiovascular disease, advantageously related to heart rhythm (preferably rhythm disorders or conduction disorders), preferably chosen among auricular and/or ventricular arrhythmia, tachycardia and/or fibrillation; for the prevention and/or treatment of diseases represented by defects in electric conduction in myocardial cells; for the prevention and/or treatment of multiple risk factors for cardiovascular disease, advantageously chosen among hypertriglyceridemia, hypercholesterolemia, hypertension, hyperlipidemia, dyslipidemia, advantageously mixed dyslipidemia, and/or factor VII hyperactivity in blood coagulation; for the treatment and/or primary or secondary prevention of cardiovascular disease derived rhythm disorders, such as auricular and/or ventricular arrhythmia, tachycardia, fibrillation and/or electrical conduction defects induced by myocardial infarction, advantageously sudden death; and/or for treatment postinfarction.

Rhythm disorders comprise in particular sinoatrial node troubles such as sinus tachycardia; atrial arrhythmia such as atrial extrasystoles, regular atrial tachycardia or auricular fibrillation; junctional tachycardia such as paroxysmal junctional tachycardia or Wolff-Parkinson-White syndrome; or ventricular arrythmia such as premature ventricular contraction, ventricular tachycardia or ventricular fibrillation.

Conduction disorders comprise in particular bradycardia.

Finally, the present invention relates to the docosahexaenoic acid ester according to the present invention, and to the pyridin-3-ylmethyl docosahexaeneoate according to the present invention, or the pharmaceutical composition according to the present invention, for use as a drug for the prevention and/or treatment of auricular fibrillation.

Without being bound by theory, it appears that the docosahexaenoic acid ester according to the present invention, in particular the pyridin-3-ylmethyl docosahexaeneoate according to the present invention, releases in the body alcohol and DHA, in particular nicotinyl alcohol and DHA in the case of pyridin-3-ylmethyl docosahexaeneoate, via esterase activity. Thus, the docosahexaenoic acid ester according to the present invention appears to have the same activity as a mixture of DHA and alcohol. Thus, if this alcohol is a group-B vitamin or provitamin, the docosahexaenoic acid ester according to the present invention will have the same effect as a mixture of DHA and a group-B vitamin or provitamin. It also appears that, in the case of pyridin-3-ylmethyl docosahexaeneoate, nicotinyl alcohol is transformed in the body into nicotinic acid. Thus, the pyridin-3-ylmethyl docosahexaeneoate according to the present invention appears to have the same activity as a mixture of DHA and nicotinic acid. The advantage of the vasodilator effect of nicotinic acid is the most satisfactory distribution of DHA in the periphery, in particular in the case of intravenous injection of pyridin-3-ylmethyl docosahexaeneoate, after conversion of nicotinyl alcohol into nicotinic acid.

The invention will be better understood in reference to the FIGURE and to the examples which follow.

FIG. 1 represents DHA-EE consumption percentage as a function of time for examples 3.1 (open tube), 3.2 (under vacuum) and 3.3 (under nitrogen bubbling) during the transesterification reaction in the presence of 200 mg of Novozyme® at 60° C. with an alcohol to ester ratio of 3.

The following are given as non-limiting examples.

REFERENCE EXAMPLE 1

Synthesis of Pyridin-3-ylmethyl Docosahexaeneoate Using $K_2CO_3$ 1 g (2.8 mmol) of ethyl docosahexaeneoate (purity higher than 95%; supplied by Interchim) is placed in 5 ml of THF degassed by nitrogen bubbling in the presence of 1.53 g (11 mmol) of ground $K_2CO_3$ and 1.06 ml (10.9 mmol) of nicotinyl alcohol (purity higher than 98%; provided by Acros). The reaction mixture is heated under reflux for 7 h and then 0.76 g (5.5 mmol) of $K_2CO_3$ is added and heating is continued for 7 h.

After cooling, the reaction mixture is taken up in water and then extracted with ethyl acetate. The organic phases are dried on $MgSO_4$, filtered and then concentrated to dryness. The residue obtained is purified by silica flash chromatography ($CH_2Cl_2 \rightarrow 90/10$ $CH_2Cl_2$/ethyl acetate gradient for 15 min). A clear oil is isolated (0.84 g, yield 71%).

Silica gel TLC 60 F 254 Merck, 90/10 $CH_2Cl_2$/AcOEt, Rf=0.35.

REFERENCE EXAMPLE 2

Synthesis of Pyridin-3-ylmethyl Docosahexaeneoate Using A Lipase

All reactions are carried out in a discontinuous mixing reactor (magnetic mixing) at the optimal temperature for each enzyme.

The products used are:
a mixture of ethyl esters enriched to 70% in DHA ethyl ester (DHA-EE) (sold by Croda Chemical Ltd.) hereafter referred to as "70% DHA-EE ester mixture;"
Novozyme®, immobilized form of *Candida antarctica* lipase sold by Novo Nordisk;
nicotinyl alcohol.

The reaction mixture is either:
a medium without solvent which uses only the substrates; or
an organic medium using various solvents.

The solvents used in this organic medium are:
2-methyl-2-butanol (2M2B), a moderately polar solvent that allows the joint solubilization of hydrophobic compounds such as polyunsaturated fatty acid esters and hydrophilic compounds such as nicotinyl alcohol; or
acetonitrile, for the same reasons as for 2M2B.

The reaction conditions are summarized in following table 1:

TABLE 1

Reaction conditions tested for the transesterification of 70% DHA-EE esters with nicotinyl alcohol.

| Alcohol | Medium | [70% DHA-EE esters] (M) | [Alcohol] | Total volume (ml) | Alcohol/ester molar ratio |
|---|---|---|---|---|---|
| Nicotinyl alcohol | Organic (2M2B and acetonitrile) | 0.43 | 0.64 | 12 | 1.5 |
| | Solvent-free | 1.5 | 4.5 | 3.5 | 3 |

Each condition was incubated with 200 mg of Novozyme® at 60° C. Reactions in 2M2B carried out in open air (under a fume hood) were tested at 60° C. with 200 mg of Novozyme®.

Regular 500 µl samples are taken until the reactions are complete. The reaction process is quenched by centrifugation for 5 minutes at 13,000 rpm, allowing withdrawal of the immobilized enzyme from the medium. All samples are stored at 4° C. until analyzed.

Control reactions without enzyme and control reactions without co-substrate (nicotinyl alcohol) were run in parallel.

Analyses are performed by using two HPLC methods (using an Agilent 1100 series apparatus) according to the following parameters:
Method 1
Zorbax SB-C18 column (4.6 mm×25 cm)
Temperature: 40° C.
Flow rate: 1 ml/min
Eluent: 0.02% methanol/acetic acid
Detection: refractometry
Run duration: 15 minutes
Method 2
Zorbax SB-C18 column (4.6 mm×25 cm)
Temperature: 40° C.
Flow rate: 3 ml/min
Eluent: 50/50 acetonitrile/acetone
Detection: refractometry
Run duration: 15 minutes The samples taken during the various reactions are diluted beforehand to a concentration less than 100 mM in a 0.02% methanol/acetic acid mixture in the case of method 1 and in acetone in the case of method 2.

Results and Discussion

Two species appear during the transesterification reaction. The first is eluted at 4.15 minutes and corresponds to the ester hydrolysis product and the second is eluted at 4.85 minutes under analysis conditions. The latter compound corresponds to the product of transesterification between the 70% DHA-EE esters and nicotinyl alcohol. Here, only one product is expected, as the nicotinyl alcohol has only a single primary hydroxyl.

The conversion percentages obtained under the various reaction conditions are given in following table 2:

TABLE 2

Conversion percentage obtained during the transesterification of 70% DHA-EE ethyl esters with nicotinyl alcohol (*: in this case, the tube is left open to allow evaporation of the ethanol produced during the reaction).

| Reaction conditions | Conversion percentages of DHA-EE into DHA-nicotinyl alcohol |
|---|---|
| Acetonitrile | 31% in 72 h |
| 2M2B | 47% in 48 h |

TABLE 2-continued

Conversion percentage obtained during the transesterification
of 70% DHA-EE ethyl esters with nicotinyl alcohol (*:
in this case, the tube is left open to allow evaporation
of the ethanol produced during the reaction).

| Reaction conditions | Conversion percentages of DHA-EE into DHA-nicotinyl alcohol |
|---|---|
| 2M2B in open air* | 60% in 118 h |
| Solvent-free | 11% in 72 h |
| Solvent-free in open air* | 100% in 72 h |

Conversion rates are higher when the reactions are carried out in open air; the ethanol produced evaporates which shifts the equilibrium of the reaction towards the synthesis of DHA-nicotinyl alcohol. These transesterification reactions are accompanied by heavy blackening of the reaction mixture.

Hydrolysis products appear preferentially when 2M2B is used as a reaction solvent. However, a weak hydrolysis reaction is also present in a medium without solvent. Thus it appears that water is also present in the nicotinyl alcohol used or that ambient moisture causes this parasitic reaction.

The feasibility of transesterification reactions of 70% DHA-EE esters with nicotinyl alcohol has been demonstrated and such reactions show advantageous conversion rates near to or greater than 90%, in particular when ethanol produced during the reaction is eliminated from the reaction mixture. However, a parasitic hydrolysis reaction due to the presence of water in the solvents used and/or to ambient moisture interferes with these syntheses.

It thus appears of interest to try to avoid the parasitic hydrolysis reaction observed. Completely anhydrous solvents could be used, for example. It is also possible to carry out these same reactions in the presence of a water trap (lithium chloride, $MgCl_2$ or silica gel, for example) to eliminate any possibility of hydrolysis.

For the nicotinyl alcohol-DHA ester synthesis reaction, ethanol produced during the reaction appears to be an element that limits the reactions. Its elimination shifts the equilibrium of the reaction towards the synthesis of the esters considered. Thus, it is advisable to optimize this elimination, notably when carrying out syntheses under reduced pressure. This allows rapid evaporation of ethanol and thus an increase in reaction speeds.

REFERENCE EXAMPLE 3

Synthesis of Pyridin-3-ylmethyl Docosahexaeneoate Using A Lipase; Transesterification Optimization; Evaporation of Ethanol Produced During the Reaction and Elimination of Oxidative Browning A synthesis reaction similar to that of example 2 was carried out using the same starting products (nicotinyl alcohol, 70% DHA-EE ester mixture, Novozyme®) in a medium without solvent at 60° C. in the presence of 200 mg of Novozyme® in an alcohol to ester ratio of 3. The reactor used is the same as that of example 2 and the analysis methods are the same.

EXAMPLE 3.1

The only difference compared to example 2 is that the reaction was carried out in an open receptacle (open tube).
Results (FIG. 1)
The transesterification reaction is "slow," taking nearly 80 hours in total. Oxidative browning is present. "Strong" parasitic hydrolysis is present.

EXAMPLE 3.2

The only difference compared to example 2 is that the reaction was carried out under vacuum.
Results (FIG. 1)
There is acceleration of the reaction compared to example 3.1 but it remains "slow," taking nearly 48 hours in total.
Additionally, oxidative browning and parasitic hydrolysis persist.

EXAMPLE 3.3

The only difference compared to example 2 is that the reaction was carried out under nitrogen bubbling.
Results (FIG. 1)
There is very significant acceleration of the reaction, which becomes total in less than 3 hours because of instantaneous elimination of the ethanol produced during the reaction and an improved mixture.
The absence of oxidative browning is noted.
Parasitic hydrolysis is strongly decreased.

EXAMPLE 4

Synthesis of DHA Ester with Panthenol Using A Lipase

The experimental and analytic conditions are the same as in example 2 except for the following differences:
Reaction conditions are summarized in following table. 3:

TABLE 3

Reaction conditions tested for the
transesterification of 70% DHA-EE esters with panthenol.

| Alcohol | Medium | [70% DHA-EE esters] (M) | [Alcohol] | Total volume (ml) | Alcohol/ester molar ratio |
|---|---|---|---|---|---|
| Panthenol | Organic (2M2B and acetonitrile) | 0.43 | 1.28 | 12 | 3 |

Results and Discussion

Two species are eluted at 3.9 minutes and 4.14 minutes under analysis conditions. Panthenol has two primary alcohols. Thus the production of several products (three maximum) could be envisaged. However, for the control without co-substrate (panthenol), the peak at 4.14 minutes appears. Said peak would thus correspond to ethyl ester hydrolysis related to the presence of water in the solvent used. This reaction is observed only in the presence of enzyme.

Consequently, only the first peak corresponds to panthenol-DHA ester synthesis.

The conversion percentages obtained under the various reaction conditions are summarized in following table 4:

TABLE 4

Conversion percentage obtained during the transesterification of 70% DHA-EE ethyl esters with panthenol (*: in this case, the tube is left open to allow evaporation of the ethanol produced during the reaction).

| Reaction conditions | Conversion percentages of DHA-EE into DHA-panthenol |
|---|---|
| Acetonitrile | 68% in 136 h |
| 2M2B | 76% in 115 h |
| 2M2B in open air* | 88% in 96 h |

It appears that the conversion percentage of 70% DHA-EE esters increases when the reaction is carried out in open air. Indeed, under this condition, the ethanol produced during the reaction evaporates. The equilibrium of the reaction is thus shifted towards the synthesis of panthenol-DHA esters. Moreover, these conversion values are certainly underestimated due to the joint evaporation of 2M2B solvent (medium concentration effect). These transesterification reactions are also accompanied by heavy blackening of the reaction mixture.

The feasibility of transesterification reactions of 70% DHA-EE esters with panthenol has been demonstrated and such reactions show advantageous conversion rates near to or greater than 90%, in particular when ethanol produced during the reaction is eliminated from the reaction mixture. However, a parasitic hydrolysis reaction due to the presence of water in the solvents used and/or to ambient moisture interferes with these syntheses.

It thus appears of interest to try to avoid the parasitic hydrolysis reaction observed. Completely anhydrous solvents could be used, for example. It is also possible to carry out these same reactions in the presence of a water trap (lithium chloride, $MgCl_2$ or silica gel, for example) to eliminate any possibility of hydrolysis.

For the panthenol-DHA ester synthesis reaction, ethanol produced during the reaction appears to be an element that limits the reactions. Its elimination shifts the equilibrium of the reaction towards the synthesis of the esters considered. Thus, it is advisable to optimize this elimination, notably when carrying out syntheses under reduced pressure. This allows rapid evaporation of ethanol and thus an increase in reaction speeds.

EXAMPLE 5

Comparative Results of the Action of EPA and DHA on Ultrarapid Potassium Current and Thus on Auricular Fibrillation The cardiac action potential is the basic electrical unit of excitable cardiac cells and represents the activity of several types of ion channels responsible for the various phases of the action potential. Different types of action potentials correspond to different cardiac regions, thus allowing sequential and coordinated activity in these regions. For this reason, Kv 1.5 potassium channels, coded by the KCNA5 gene, are expressed only in auricle tissue and are responsible for the ultrarapid potassium current ($I_{Kur}$) which acts in the repolarization of the auricular action potential. This highly localized expression of Kv 1.5 is in fact a target of choice in the treatment of auricular fibrillation, a pathology in which changes in auricular action potentials are observed.

Thus, the effects of DHA and EPA on $I_{Kur}$ were studied. For this purpose, the human isoform of the Kv 1.5 channel (hKv 1.5) was transfected in a stable manner in HEK 293 (human embryonic kidney) cells and the current resulting from the activity of these channels was studied using a whole-cell patch-clamp technique.

Materials and Methods
Maintenance of the Cell Line

HEK 293-hKv 1.5 cells are grown under standard conditions (37° C., incubator at 95% $O_2$ and 5% $CO_2$) in Falcon dishes up to 80% confluence. They are then removed and cultured in 35 mm petri dishes containing the following culture medium: DMEM (Invitrogen); 10% fetal bovine serum (Invitrogen); a mixture of 100 U/ml penicillin, 100 µg/ml streptomycin and 0.25 mg/ml glutamine (Invitrogen); and 1.25 mg/ml of Geneticin® as a selective antibiotic.

Electrophysiology $I_{Kur}$ is studied using the whole-cell patch-clamp technique at ambient temperature (19-22° C.). The pipette medium contains: 125 mM K-aspartate, 20 mM KCl, 10 mM EGTA, 5 mM HEPES, 5 mM Mg-ATP, 1 mM $MgCl_2$, pH 7.3 (KOH). The extracellular medium contains: 140 mM NaCl, 20 mM HEPES, 5 mM D(+)-glucose, 5 mM KCl, 2 mM $CaCl_2$, 1 mM $MgCl_2$, pH 7.4 (NaOH).

$I_{Kur}$ is induced every 15 seconds by 300 ms, +60 mV depolarizing pulses from a −80 mV holding potential, followed by −50 mV repolarization. The amplitude of the current peak is established from the maximum current obtained during the first 100 ms of the depolarizing pulse. The amplitude of the current at the end of the pulse is determined during the last 20 ms of the depolarizing pulse.

Reagents

DHA and EPA are supplied by Sigma. Stock solutions (10 mM) are prepared in ethanol and the final concentration of solvent is 0.25%.

Results

Results are summarized in following table 5.

TABLE 5

Percent inhibition of $I_{Kur}$ by DHA and EPA at various concentrations.

| Concentration | Peak $I_{Kur}$ | | End of pulse $I_{Kur}$ | | n |
|---|---|---|---|---|---|
| | Mean | SEM | Mean | SEM | |
| DHA | | | | | |
| 1 µM | 8.2 | 6.3 | 10.1 | 5.8 | 5 |
| 3.2 µM | 10.9 | 6.9 | 14.5 | 6.5 | 5 |
| 5.6 µM | 15.4 | 4.8 | 33.7 | 7.8 | 6 |
| 10 µM | 22.6 | 4.0 | 78.0 | 4.2 | 6 |
| 25 µM | 58.1 | 13.6 | 86.5 | 3.4 | 5 |
| EPA | | | | | |
| 1 µM | 14.6 | 1.7 | 14.9 | 1.9 | 5 |
| 3.2 µM | 16.1 | 3.1 | 19.9 | 4.4 | 5 |
| 10 µM | 17.5 | 6.4 | 36.6 | 7.2 | 10 |
| 25 µM | 5.4 | 6.8 | 61.6 | 7.3 | 5 |

EPA slightly decreases peak $I_{Kur}$ amplitude (maximum inhibition of 17.5±6.4%, n=10, p<0.05 at 10 µM) and end-of-pulse current amplitude (61.6±7.3%, n=5, p<0.05 at 25 µM).

DHA inhibits peak $I_{Kur}$ amplitude by a maximum of 58.1±13.6% (n=5, p<0.005) and that of end-of-pulse current amplitude by 86.5±3.4% (n=5, p<0.005) at 25 µM.

Conclusion

These results show that the application of DHA inhibits, more strongly than EPA and in a concentration-dependant manner, the ultrarapid potassium current ($I_{Kur}$) of human Kv 1.5 channels transfected in HEK 293 cells. DHA acts preferentially on end-of-pulse current, suggesting an effect on the inactivation of Kv 1.5 channels. Moreover, this effect is accompanied by a decrease in peak $I_{Kur}$ (contrary to that observed for EPA), potentiating $I_{Kur}$ inhibition by DHA.

These effects on $I_{Kur}$ indicate a beneficial action of DHA on auricular fibrillation.

The invention claimed is:

1. A docosahexaenoic acid ester with an alcohol chosen among the group consisting of:

panthenol of the following formula:

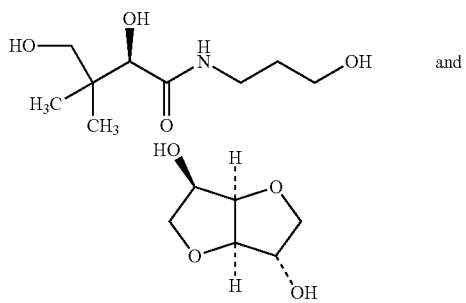

and isosorbide of the following formula:
and isosorbide mononitrate of the following formula:

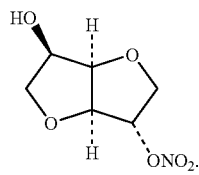

2. A method of preparation of docosahexaenoic acid ester according to claim 1 which comprises the step of transesterification of docosahexaenoic acid ethyl ester with the alcohol chosen among the group consisting of panthenol, isosorbide, and isosorbide mononitrate.

3. A method according to claim 2, wherein said method is carried out in the presence of a catalyst.

4. A method according to claim 3, wherein the catalyst is a lipase.

5. A method according to claim 4, wherein ethanol is eliminated during the reaction.

6. A method according to claim 4, wherein the reaction takes place in an anhydrous solvent or without solvent in a dry atmosphere.

7. A pharmaceutical composition comprising docosahexaenoic acid ester according to claim 1 and at least one pharmaceutically-acceptable excipient.

8. A method for the treatment of cardiovascular diseases related to heart rhythm, for the treatment of diseases represented by defects in electric conduction in myocardial cells; for the treatment of multiple risk factors for cardiovascular disease chosen among hypertriglyceridemia, hypertension, hyperlipidemia dyslipidemia; for the treatment of cardiovascular disease derived from heart rhythm disorders, and/or for treatment postinfarction comprising the administration of an effective amount of docosahexaenoic acid ester according to claim 1 or pyridin-3-ylmethyl docosahexaenoate, or of a pharmaceutical composition according to claim 7, to a patient in need thereof.

9. A method for the treatment of auricular fibrillation comprising the administration of an effective amount of docosahexaenoic acid ester according to claim 1, or of pyridin-3-ylmethyl docosahexaenoate, or of a pharmaceutical composition according to claim 7 to a patient in need thereof.

10. The method according to claim 8 wherein the cardiovascular diseases related to heart rhythm are chosen among auricular and/or ventricular arrhythmia, tachycardia and/or fibrillation.

11. The method according to claim 8 wherein the cardiovascular diseases derived from heart rhythm disorders are chosen among auricular and/or ventricular arrhythmia, tachycardia, fibrillation and/or electrical conduction defects induced by myocardial infarction.

12. The method according to claim 11 wherein the cardiovascular disease derived from heart rhythm disorders is sudden death.

13. Docosahexaenoic acid ester with panthenol.

* * * * *